US005674718A

United States Patent [19]
Michel-Briand et al.

[11] Patent Number: 5,674,718
[45] Date of Patent: Oct. 7, 1997

[54] DNA SEGMENTS AND TRANSFORMED MICROORGANISMS COMPRISING THE DELTA[1]-DEHYDROGENASE GENE PSEUDOMONAS TESTOSTERONI, AND USES THEREOF

[75] Inventors: Yvon Michel-Briand, Besançon; Patrick Plesiat, Roche-Lez-Beaupre, both of France

[73] Assignee: Roussel Uclaf, France

[21] Appl. No.: 200,512

[22] Filed: Feb. 17, 1994

Related U.S. Application Data

[63] Continuation of Ser. No. 768,660, filed as PCT/FR91/00094, Feb. 7, 1991, abandoned.

[30] Foreign Application Priority Data

Feb. 7, 1990 [FR] France ................................ 90 01399

[51] Int. Cl.[6] .......................... C12N 15/53; C12N 15/63; C12N 15/78; C12P 7/26
[52] U.S. Cl. .................. 435/147; 536/23.2; 536/23.7; 536/24.32; 435/252.3; 435/252.34; 435/320.1; 435/14; 435/29; 435/72; 435/60

[58] Field of Search ................... 536/23.2, 23.7, 536/24.72; 435/69.1, 252.3, 252.33, 252.34, 320.1, 147

[56] References Cited

U.S. PATENT DOCUMENTS

| | | | |
|---|---|---|---|
| 4,647,529 | 3/1987 | Rodland et al. | 435/6 |
| 5,082,785 | 1/1992 | Manning et al. | 435/252.32 |

OTHER PUBLICATIONS

Kuliopulos et al (1987) Proc. Natl Acad. Sci 84, 8893–8897.
Eaton et al (1986) J. Bacteriol. 168(1), 123–131.
Levy et al (1959) J. Biol. Chem 234, 2014–2021.
Plesiat et al. J. Bacteriol. 173, 7219–7227.
Mermod, N., et al., 1986, Journal of Bacteriology, 167(2): 447–454.

*Primary Examiner*—Robert A. Wax
*Assistant Examiner*—William W. Moore
*Attorney, Agent, or Firm*—Bierman & Muserlian

[57] ABSTRACT

Nucleic acids segment comprising a nucleotide coding sequence for *Pseudomonas testosteroni* Δ1-dehydrogenase or an homologous or complementary nucleotide sequences thereof.

12 Claims, No Drawings

DNA SEGMENTS AND TRANSFORMED MICROORGANISMS COMPRISING THE DELTA¹-DEHYDROGENASE GENE PSEUDOMONAS TESTOSTERONI, AND USES THEREOF

This is a continuation of Ser. No. 768,660, filed as PCT/FR91/00094, Feb. 7, 1991, now abandoned.

The present invention relates to the cloning of the Pseudomonas testosteroni delta¹-dehydrogenase gene, to the coding sequence for said gene, as well as to the microorganisms transformed by the introduction of said gene and to their use for the production of delta¹-dehydrogenase and for the synthesis and analysis of steroid substances The biotransformation of steroids by microorganisms, or by enzymes derived from the latter, with the object of synthesizing medicaments, is commonly used in the pharmaceutical industry, due to the very high specificity and low cost price of reactions carried out in this way.

For example, the delta¹-dehydrogenase obtained from certain Athrobacter strains is commonly used in the synthesis of sterols for therapeutic use, such as, for example, prednisone and prednisolone, starting from substrates such as, for example, cortisone or hydrocortisone.

Pseudomonas testosteroni is a gram-negative bacterium, found in soil, and which is capable of growing using sterols as the only source of carbon. This organism completely degrades sterols, and several enzymes are involved in this metabolism:

3-(or 17)-beta-hydroxysteroid-dehydrogenase (EC 1.1.1.51) also known under the name of beta-enzyme, 3-alpha-hydroxysteroid-dehydrogenase (EC 1.1.1.50) also known under the name of alpha-enzyme, 3-oxosteroid delta4-delta5-isomerase (EC 5.3.3.1) also known under the name of isomerase, 3-oxosteroid delta-1-dehydrogenase (EC 1.3.99.4) also known under the name of delta¹-dehydrogenase, as well as two other dehydrogenases (EC 1.3.99.5 and EC 1.3.99.6).

The *Pseudomonas testosteroni* delta¹-dehydrogenase has, relative to enzymes of the same type currently being used, the advantage of high physico-chemical stability.

Attempts to isolate and characterize this enzyme have been carried out, [LEVY and TALALAY, Journal of biological Chemistry (1959), 234, 2014–2021]; however, they have not resulted in the complete purification of the protein, the sequence of which still remains unknown.

Moreover, due to the complexity of the sterol metabolism of *Pseudomonas testosteroni* and the different enzymes involved in said metabolism, it is impossible to directly use *Pseudomonas testosteroni* in industry for specific synthetic reactions.

Consequently inventors have aimed at isolating and cloning the *Pseudomonas testosteroni* delta¹-dehydrogenase gene, in such a way so as to allow, on the one hand the expression of said gene in an appropriate host, such as a bacterium for industrial use, and on the other hand the delta¹-dehydrogenase to be obtained in a purified form.

Therefore a subject of the present invention is nucleic acid segments, characterized in that they contain at least one nucleotide sequence chosen from the group constituted by:

a) a nucleotide coding sequence for *Pseudomonas testosteroni* delta¹-dehydrogenase, b) a nucleotide sequence regulating the expression of the *Pseudomonas testosteroni* delta¹-dehydrogenase gene, c) the homologous or complementary nucleotide sequences of all or part of one or other of the sequences defined in a) or b).

According to the present invention, "homologous sequence" means, not only sequences identical to those defined in a) or b), or to a segment of these, but also those that differ only by the substitution, the deletion or the addition of a certain number of nucleotides, provided that the sequences thus modified are functionally equivalent to the sequence or segment considered.

Similarly, "complementary sequence" means, not only sequences which are strictly complementary to the sequences defined in a) or b) or its segments, but also modified sequences as indicated previously, provided that they are functionally equivalent to said strictly complementary sequences.

Such functionally equivalent sequences are for example:

DNA sequences which are able to specifically hybridize with the delta¹-dehydrogenase gene, which can be used to obtain probes which allow the selection of recombinants having integrated said gene, during the cloning of the latter.

DNA coding sequences for P. testosteroni delta¹-dehydrogenase, and derivatives of sequence (I) which is defined hereafter following the actual description, by replacement of one or more codons of said sequence (I) by other codons whose translation product is identical.

DNA segments which conform to the invention can be obtained either by any one of the techniques used in molecular biology or genetic engineering, or by the combination of several of these techniques.

Said techniques include, without this constituting a limitative list, extraction and purification techniques for nucleic acids, techniques for the fragmentation of nucleic acid molecules by restriction enzymes or by any other appropriate method, techniques for the synthesis or hemisynthesis of nucleic acids, techniques for the mutagenesis or transformation of microorganisms, techniques for the labelling or hybridization of probes, recombination techniques for nucleic acids, etc.

According to a preferred method for producing a DNA segment conforming to the invention, it contains at least one sequence which is homologous or complementary to sequence (I) (designated in the attached list of sequences under the No. SEQ IDNO:1), and which is that of the KpnI fragment of about 2.2 kb, of Pseudomonas testosteroni DNA.

In a particularly advantageous manner, a DNA segment conforming to the invention contains a coding sequence for P. testosteroni delta¹-dehydrogenase, which sequence begins at nucleotide 248 and finishes at nucleotide 1966 of sequence (I).

Also a subject of the present invention is recombinant vectors, characterized in that they contain a nucleic acid segment conforming to the invention, as defined above.

By recombinant vector is meant a nucleic acid sequence resulting from the recombination of a nucleic acid sequence capable of self-replicating, and a nucleic acid sequence that one wishes to clone and amplify. Said recombinant vectors can also be expression vectors, carrying nucleotide sequences that control the transcription and translation of a coding sequence inserted in an appropriate site of said vector.

In an advantageous manner, said vectors contain moreover, sequences which ensure the regulation of expression of this gene such as, for example, sequences allowing control over the expression of said gene as a function of the conditions of the ambient environment, such as for example the temperature.

According to a preferred method of implementing the present invention, a recombinant vector is constituted by the plasmid called pTEK21, which plasmid results from the insertion of the 2.2 kb DNA segment defined above into the plasmid pUC18.

According to another preferred method of implementing the present invention, such an expression vector is constituted by the recombinant plasmid called pLE689, which results from the insertion in the plasmid pNM185 of the nucleotide coding sequence for *Pseudomonas testosteroni* delta$^1$-dehydrogenase, combined with other nucleotide sequences derived from the *Pseudomonas Testosteroni* genome, sequences which play a role in the expression and/or in the regulation of expression of the delta$^1$-dehydrogenase gene.

The plasmid pNM185 is described in the publication MERMOD and al., [*J. Bacteriol.*, 167:447–454 (1986)].

Also a subject of the present invention is microorganisms transformed by one of the recombinant vectors defined above.

The clones of *Escherichia Coli, Pseudomonas putida*, and *Pseudomonas aeruginosa*, transformed by the vectors mentioned above, are the subject of a deposition with the Collection Nationale de Cultures de Micro-organismes (CNCM), on the 24th January 1990:

the *E. coli* clone DH5alpha transformed by the plasmid pTEK21 has the deposition number I-922;

the *E. coli* clone RR1 transformed by the plasmid pLE689 has the deposition number I-923;

the *P. putida* clone KT2440 transformed by the plasmid pLE689 has the deposition number I-924;

the *P. aeruginosa* clone PAO1161 transformed by the plasmid pLE689 has the deposition number I-925;

The microorganisms transformed by any one of the plasmids which conform to the invention can be used for cloning and amplifying said plasmid, which carries the *Pseudomonas testosteroni* delta$^1$-dehydrogenase gene. Moreover, appropriate microorganisms, transformed by a plasmid capable of replicating in the former and allowing the expression of the delta$^1$-dehydrogenase gene, can be used, advantageously, in the biotransformation of steroids, because the delta$^1$-dehydrogenase activity expressed by these microorganisms is not contaminated by other steroid degradation activities.

Also a subject of the present invention is nucleic acid probes allowing the detection of the delta$^1$-dehydrogenase gene, or of a related gene, in *Pseudomonas testosteroni*, or in other microorganisms carrying such a gene, which probes are characterized in that they contain at least one of the nucleic acid segments conforming to the invention, as have been defined previously, combined with at least one appropriate means of detection.

In addition a subject of the present invention is a polypeptide chain containing a sequence of amino acids derived from the nucleotide coding sequence for the *Pseudomonas testosteroni* delta$^1$-dehydrogenase.

Moreover a subject of the present invention is a preparation process for *Pseudomonas testosteroni* delta$^1$-dehydrogenase, which process is characterized in that it consists of the following stages:

a) a microorganism culture containing a vector allowing the expression of the *Pseudomonas testosteroni* delta$^1$-dehydrogenase gene, b) isolation of the enzyme product from said culture.

The delta$^1$-dehydrogenase purified in this way can be advantageously used for the analysis or biosynthesis of steroids.

The present invention will be better understood with the assistance of the following additional description, which refers to examples of the preparation of nucleic acid segments conforming to the invention. It must be understood, however, that these examples are given solely as an illustration of the subject of the invention, of which they in no way constitute a limitation.

I) PURIFICATION AND CLONING OF SEGMENTS CARRYING THE CODING SEQUENCE FOR *PSEUDOMONAS TESTOSTERONI* DELTA$^1$-DEHYDROGENASE.

Example 1

Preparation of a probe allowing the localization of the coding sequence of *Pseudomonas testosteroni* delta$^1$-dehydrogenase.

This probe was obtained from the DNA of mutant derivatives of the P. testosteroni strain designated by the number ATCC 17410.

a) Mutagenesis

The mutagenesis of the *P. testosteroni* strain ATCC 17410 is carried out by using the transposon Tn5 carrying a kanamycine resistance gene, inserted in the suicide vector pSUP2021. This vector is transferred from *E. coli* 17–1. During the conjugation between *E. coli* 17–1 and *P. testosteroni* ATCC 17410, the transfer of the vector pSUP2021 occurs with a high frequency.

The selection of *P. testosteroni* clones containing the transposon TN5 is carried out on a minimum culture medium (medium M9) containing 5 mM of sodium parahydroxybenzoate, and 50 microgrammes/ml of kanamycine.

5200 clones of the ATCC 17410 strain, which are resistant to kanamycine are isolated. From these clones, 41 which do not use testosterone as the sole carbon source are selected. One of these 41 clones (clone 06) has a very weak delta$^1$-dehydrogenase activity.

The total DNA of clone 06 is extracted and hydrolyzed with EcoRI. The EcoRI fragments thus obtained were inserted in pUC19 according to the random religation procedure with ligase T4. The ligation mixture thus obtained serves to transform competent cells of *E. coli* DH5alpha [provided by GIBCO BRL, 14, rue des Oziers-95051CERGY PONTOISE CEDEX]. The bacterial clones containing the transposon Tn5 are selected according to their resistance to kanamycine. One of these clones, the carrier of a recombinant plasmid pUC19 containing an EcoRI insert of approximately 14 kb is chosen.

A BamHI-EcoRI fragment of 0.8 kb, adjacent to Tn5 is selected for use as a probe. This fragment is sub-cloned in plasmid pUC19 according to the following procedure: hydrolysis of the 14 kb EcoRI insert using BamHI, separation of the BamHI-EcoRI fragment by electrophoresis in an agarose gel, purification by electroelution of the gel, then labelling with [$^{32}$p] dCTP by the so-called method of nick translation.

Example 2

Obtaining a 8.3 kb fragment carrying the delta$^1$-dehydrogenase gene.

The total DNA of *Pseudomonas testosteroni* is extracted by precipitation in ethanol after lysis of the bacterium by SDS. This DNA is hydrolyzed with the restriction enzyme SalI under the following conditions: incubation of the DNA with the enzyme, at 37° C. for 2 hours, at the rate of 3 units per microgram of DNA.

The fragments obtained are inserted in plasmid pUC19, by the action of ligase T4.

The recombinant plasmids obtained are used to transform the bacterial strain *E. coli* DH5alpha under conditions defined by GIBCO BRL, supplier of competent cells. The bank thus obtained is coliformed by hybridization with the 0.8 kb probe obtained according to the procedure described in Example 1.

5 clones containing a SalI fragment of 8.3 kb are obtained in this way.

Example 3

Preparation of plasmid pTEK21.

Sub-cloning of the 2.1 kb KpnI fragment starting from the 8.3 kb SalI fragment: the 8.3 kb fragment is hydrolyzed by the enzyme KpnI. The 2.1 kb fragment released is separated by electrophoresis in an agarose gel and purified. It is then religated in a vector pUC18, which has been linearized beforehand with KpnI.

The presence of the delta$^1$-dehydrogenase gene on this 2.1 kb fragment is proven by the detection of products resulting from the action of this enzyme. The operating protocol used for this detection is explained in detail further on (Example 3).

II) SEQUENCING OF THE *PSEUDOMONAS TESTOSTERONI* DELTA$^1$-DEHYDROGENASE GENE.

The sequencing of the 2.1 kb KpnI fragment is carried out using the SANGER method of enzymatically labelling with dideoxynucleotides in the presence deoxyribonucleotides labelled with [35S].

III) PROVING THE EXPRESSION OF THE *PSEUDOMONAS TESTOSTERONI* DELTA1-DEHYDROGENASE GENE IN TRANSFORMED BACTERIAL CELLS.

The *E. coli* DH5alpha strain containing the recombinant plasmid pTEK21 is cultivated in a nutritive broth at 30° C., in the presence of a substrate of the delta$^1$-dehydrogenase (1.75 mM of delta$^4$-androstene-3,17-dione). After incubation for 16 hrs, the steroids are extracted with ethyl acetate and analyzed by thin layer chromatography on silica, using a solvent mixture of dichloromethane/dioxan. The delta$^1$-dehydehydrogenated metabolite (delta$^{1,4}$-androstadiene-3, 17-dione) appears under ultra-violet light as a characteristic stain.

Much as it pertains to what has gone before, the invention is not at all limited to those of its methods of implementation, production and use which have just been described more explicitly; on the contrary it encompasses all the variants that can occur to a man skilled in the art, without diverging from the scope, nor the range, of the present invention.

---

What is claimed is:

1. An isolated nucleic acid segment comprising a nucleotide coding sequence encoding a *Pseudomonas testosteroni* delta$^1$-dehydrogenase having the nucleotide sequence set forth in SEQ ID NO:1.

2. An isolated nucleic acid segment of claim 1 having a coding sequence for *Pseudomonas testosteroni* delta$^1$-dehydrogenase, which sequence begins at nucleotide 248 and finishes at nucleotide 1966 of the nucleotide sequence set forth in SEQ ID No.: 1.

3. A recombinant vector comprising a nucleic acid segment of claim 2.

4. A recombinant vector of claim 3 which is the plasmid pTEK21 resulting from the insertion of a DNA segment comprising the nucleotide sequence set forth in SEQ ID No.: 1 in the plasmid pUC18.

5. A recombinant vector of claim 3 consisting of an insertion in the plasmid vector pMN 185 of a nucleic acid segment comprising a nucleotide sequence encoding a *Pseudmonas testosteroni* delta$^1$-dehydrogenase together with further nucleotide sequences native to the *Pseudomonas testosteroni* genome.

6. A transformed microorganism clone having at least one recombinant vector of claim 3.

7. A clone of claim 6 filed at the Collection Nationale de Cultures de Microorganismes (CNCM) under the No. I-922, and constituted by bacterial cells of the *E. coli* DH5 α strain, containing the plasmid pTEK21.

8. A clone of claim 6 filed at the Collection Nationale de Cultures de Microorganismes (CNCM) under the No. I-923, and constituted by bacterial cells of the *E. coli* RR1 strain, containing the plasmid pLE689.

9. A clone of claim 6 filed at the Collection Nationale de Cultures de Microorganismes (CNCM) under the No. I-924, constituted by bacterial cells of the *P. putida* KT2440 strain, containing the plasmid pLE689.

10. A clone of claim 6 filed at the Collection Nationale de Cultures de Microorganismes (CNCM) under the No. I-925, and constituted by bacterial cells of the *P. aeruginosa* PA1161 strain, containing the plasmid pLE689.

11. In a method for the biotransformation of steroids, the improvement comprising using a microorganism transformed by a recombinant vector of claim 3.

12. A hybridization detection probe comprising at least one nucleic acid segment of claim 2 combined with at least one means of detection.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 2230 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE:
        ( A ) DESCRIPTION: GENOMIC DNA ( i i i ) HYPOTHETICAL: NO ( i v ) ANTI-SENSE: NO ( v ) ORIGINAL SOURCE:
        ( A ) ORGANISM: PSEUDOMONAS TESTOSTERONI ( v i i ) FEATURE:
        ( A ) NAME/KEY: mat_peptide
        ( B ) LOCATION: 248..1966
        ( C ) IDENTIFICATION METHOD: EXPERIMENTAL
        ( D ) OTHER INFORMATION: /function = coding
            gene for P. testosteroni delta-
            dehydrogenase ( v i i i ) SEQUENCE DESCRIPTION:SEQ ID NO:1:

```
GGTACCTTCA  AGAACAATCC  CATCGAGCGC  ATCTTCCGCG  ACATCCATCA           50

GGGACGTACC  CACATTGCGA  ACAATACGGA  TGCCTATGTG  CGCGCCTATG          100
```

-continued

```
GCTCGCATGT GCTGGGATTC CCAACCAGGA ACCTTTTGTC TGATTGAATT      150

CATGCAGCAA GCTGCGGCAG CGCTCCCATA ACGGAGGCTG CCGCCAGCTG      200

TATTTGCGAC AGTCCATCCA TAAAACAAAG ATTGACGGAG ACAAGGT ATG    250
                                                        Met
                                                         1
```

| | | | | | | | | | | | | |
|---|---|---|---|---|---|---|---|---|---|---|---|---|
| GCA | GAA | CAA | GAA | TAT | GAC | CTG | ATC | GTC | GTG | GGT | TCG | GGG | 289
| Ala | Glu | Gln | Glu | Tyr | Asp | Leu | Ile | Val | Val | Gly | Ser | Gly |
|     |     |     | 5   |     |     |     |     | 10  |     |     |     |     |
| GCA | GGT | GCC | TGT | TGG | GCG | CCA | ATT | CGC | GCG | CAG | GAG | CAG | 328
| Ala | Gly | Ala | Cys | Trp | Ala | Pro | Ile | Arg | Ala | Gln | Glu | Gln |
| 15  |     |     |     |     | 20  |     |     |     |     | 25  |     |     |
| GGC | CTC | AAG | ACT | CTG | GTG | GTG | GAG | AAG | ACC | GAG | CTG | TTC | 367
| Gly | Leu | Lys | Thr | Leu | Val | Val | Glu | Lys | Thr | Glu | Leu | Phe |
|     |     | 30  |     |     |     |     | 35  |     |     |     |     | 40  |
| GGT | GGC | ACT | TCG | GCT | CTG | TCG | GGG | GGT | GGT | ATC | TGG | ATT | 406
| Gly | Gly | Thr | Ser | Ala | Leu | Ser | Gly | Gly | Gly | Ile | Trp | Ile |
|     |     |     |     | 45  |     |     |     |     | 50  |     |     |     |
| CCG | CTC | AAT | TAC | GAC | CAG | AAG | ACC | GCT | GGC | ATC | AAA | GAC | 445
| Pro | Leu | Asn | Tyr | Asp | Gln | Lys | Thr | Ala | Gly | Ile | Lys | Asp |
|     |     | 55  |     |     |     |     | 60  |     |     |     |     | 65  |
| GAT | CTG | GAA | ACC | GCA | TTT | GGC | TAT | ATG | AAG | CGC | TGT | GTG | 484
| Asp | Leu | Glu | Thr | Ala | Phe | Gly | Tyr | Met | Lys | Arg | Cys | Val |
|     |     |     | 70  |     |     |     |     | 75  |     |     |     |     |
| CGC | GGC | ATG | GCA | ACC | GAC | GAC | CGC | GTG | CTG | GCC | TAT | GTG | 523
| Arg | Gly | Met | Ala | Thr | Asp | Asp | Arg | Val | Leu | Ala | Tyr | Val |
| 80  |     |     |     |     | 85  |     |     |     |     | 90  |     |     |
| GAA | ACC | GCG | AGC | AAG | ATG | GCC | GAG | TAC | CTG | CGC | CAG | ATC | 562
| Glu | Thr | Ala | Ser | Lys | Met | Ala | Glu | Tyr | Leu | Arg | Gln | Ile |
|     |     |     | 95  |     |     |     |     | 100 |     |     |     | 105 |
| GGC | ATC | CCT | TAT | CGC | GCC | ATG | GCC | AAG | TAT | GCG | GAC | TAC | 601
| Gly | Ile | Pro | Tyr | Arg | Ala | Met | Ala | Lys | Tyr | Ala | Asp | Tyr |
|     |     |     |     | 110 |     |     |     |     | 115 |     |     |     |
| TAC | CCC | CAT | ATC | GAA | GGC | TCC | AGG | CCC | GGT | GGC | CGC | ACC | 640
| Tyr | Pro | His | Ile | Glu | Gly | Ser | Arg | Pro | Gly | Gly | Arg | Thr |
|     |     | 120 |     |     |     |     | 125 |     |     |     |     | 130 |
| ATG | GAC | CCG | GTG | GAC | TTC | AAT | GCC | GCC | AGG | CTG | CGC | GTG | 679
| Met | Asp | Pro | Val | Asp | Phe | Asn | Ala | Ala | Arg | Leu | Arg | Val |
|     |     |     |     | 135 |     |     |     |     | 140 |     |     |     |
| ACG | GCA | CTG | GAA | ACC | ATG | CGC | CCC | GGC | CCT | CCC | GGC | AAC | 718
| Thr | Ala | Leu | Glu | Thr | Met | Arg | Pro | Gly | Pro | Pro | Gly | Asn |
| 145 |     |     |     |     | 150 |     |     |     |     | 155 |     |     |
| CAG | TTG | TTC | GGC | CGC | ATG | AGC | ATC | AGT | GCC | TTC | GAG | GCG | 757
| Gln | Leu | Phe | Gly | Arg | Met | Ser | Ile | Ser | Ala | Phe | Glu | Ala |
|     |     | 160 |     |     |     |     | 165 |     |     |     |     | 170 |
| CAT | TCC | ATG | CTC | TCG | CGC | GAG | CTC | AAG | TCG | CGC | TTC | ACC | 796
| His | Ser | Met | Leu | Ser | Arg | Glu | Leu | Lys | Ser | Arg | Phe | Thr |
|     |     |     |     | 175 |     |     |     |     | 180 |     |     |     |
| ATC | CTG | GGC | ATC | ATG | CTC | AAG | TAT | TTT | CTG | GAC | TAC | CCC | 835
| Ile | Leu | Gly | Ile | Met | Leu | Lys | Tyr | Phe | Leu | Asp | Tyr | Pro |
|     |     |     |     | 185 |     |     |     | 190 |     |     |     | 195 |
| TGG | CGC | AAC | AAG | ACC | AGG | CGC | GAT | CGT | CGC | ATG | ACG | GGC | 874
| Trp | Arg | Asn | Lys | Thr | Arg | Arg | Asp | Arg | Arg | Met | Thr | Gly |
|     |     |     |     | 200 |     |     |     |     | 205 |     |     |     |
| GGC | CAG | GCG | CTG | GTG | GCA | GGC | CTG | CTG | ACT | GCT | GCC | AAC | 913
| Gly | Gln | Ala | Leu | Val | Ala | Gly | Leu | Leu | Thr | Ala | Ala | Asn |
| 210 |     |     |     |     | 215 |     |     |     |     | 220 |     |     |
| AAG | GCC | CGC | GTC | GAG | ATG | TGG | TGC | AAC | TCT | CCG | CTC | AAG | 952
| Lys | Ala | Arg | Val | Glu | Met | Trp | Cys | Asn | Ser | Pro | Leu | Lys |
|     |     | 225 |     |     |     |     | 230 |     |     |     |     | 235 |

```
GAG CTG GTG CAG GAT GCA TCG GGC CGC GTG ACG GGT GTC        991
Glu Leu Val Gln Asp Ala Ser Gly Arg Val Thr Gly Val
            240                 245

ATT GTT GAG AGG AAT GGT CAG CGC CAG CAG ATC AAC GCC        1030
Ile Val Glu Arg Asn Gly Gln Arg Gln Gln Ile Asn Ala
        250                 255                 260

AGA CGT GGC GTG TTG TTG GGT GCA GGC GGT TTT GAG CGC        1069
Arg Arg Gly Val Leu Leu Gly Ala Gly Gly Phe Glu Arg
                265                 270

AAT CAG GAG ATG CGT GAC CAG TAT CTG AAC AAG CCC ACA        1108
Asn Gln Glu Met Arg Asp Gln Tyr Leu Asn Lys Pro Thr
275             280                 285

AGG CTG GTG GAC GGC AAC CCC TGT GGG AGG CAA TAC GGT        1147
Arg Leu Val Asp Gly Asn Pro Cys Gly Arg Gln Tyr Gly
            290                 295                 300

GAT GCT CAC CGG GCC GGT CAG GCG TGG GCG CAC ACT GGC        1186
Asp Ala His Arg Ala Gly Gln Ala Trp Ala His Thr Gly
                305                 310

GCT GAT GGA CTG GTC CTG GGG CGT GCC CAC CAT GGA TGT        1225
Ala Asp Gly Leu Val Leu Gly Arg Ala His His Gly Cys
315             320                 325

TCC CAA GGA GCC GGC CTT TCG CGG CAT TTT CGT GGA ACG        1264
Ser Gln Gly Ala Gly Leu Ser Arg His Phe Arg Gly Thr
            330                 335

CTC GCT GCC GGG GTG CAT GGT GGT CAA CGA CAA GGG GCA        1303
Leu Ala Ala Gly Val His Gly Gly Gln Arg Gln Gly Ala
340             345                 350

GCG CTT CCT CAA CGA GTC CGG CCC GTA TCC GGA ATT CCA        1342
Ala Leu Pro Gln Arg Val Arg Pro Val Ser Gly Ile Pro
        355                 360                 365

GCA GCC ATG CTG GCC GAA AAT GCC AAG GGC AAT GGC GGT        1381
Ala Ala Met Leu Ala Glu Asn Ala Lys Gly Asn Gly Gly
                370                 375

GTG CCT GCA TGG ATT GTG TTC GAC GCC AGC TTC CGC GCG        1420
Val Pro Ala Trp Ile Val Phe Asp Ala Ser Phe Arg Ala
380             385                 390

CAA AAC CCC ATG GGG CCG CTG ATG CCA GGC TCG GCC GTG        1459
Gln Asn Pro Met Gly Pro Leu Met Pro Gly Ser Ala Val
            395                 400

CCA GAC AGC AAG GTG CGC AAG AGC TGG CTG AAC AAT GTC        1498
Pro Asp Ser Lys Val Arg Lys Ser Trp Leu Asn Asn Val
405             410                 415

TAC TGG AAG GGC AGA CGC TGG AAG ATC TGG CGC GCA GAT        1537
Tyr Trp Lys Gly Arg Arg Trp Lys Ile Trp Arg Ala Asp
        420                 425                 430

CGG CGT GGA CGT GCT GGG CTG CAG GTC AGT GCG CGT CGC        1576
Arg Arg Gly Arg Ala Gly Leu Gln Val Ser Ala Arg Arg
                435                 440

ATG ACC GAA TAC GCC AGA GCT GGC AAG GAC CTG GAC TTT        1615
Met Thr Glu Tyr Ala Arg Ala Gly Lys Asp Leu Asp Phe
445             450                 455

GAC CGG GGC GGC AAT GTG TTT GAC CGC TAC TAC GGC GAT        1654
Asp Arg Gly Gly Asn Val Phe Asp Arg Tyr Tyr Gly Asp
        460                 465

CCG CGT CTC AAG AAT CCC AAC CTG GGT CCC ATC GAG AAA        1693
Pro Arg Leu Lys Asn Pro Asn Leu Gly Pro Ile Glu Lys
470             475                 480

GGT CCG TTC TAC GCC ATG CGT CTG TGG CCC GGT GAG ATC        1732
Gly Pro Phe Tyr Ala Met Arg Leu Trp Pro Gly Glu Ile
        485                 490                 495
```

|     |     |     |     |     |     |     |     |     |     |     |     |      |
|-----|-----|-----|-----|-----|-----|-----|-----|-----|-----|-----|-----|------|
| GGC | ACC | AAG | GGG | GGG | CTG | CTG | ACC | GAC | AGG | GAA | GGC | CGT  | 1771
| Gly | Thr | Lys | Gly | Gly | Leu | Leu | Thr | Asp | Arg | Glu | Gly | Arg  |
|     |     |     | 500 |     |     |     |     |     | 505 |     |     |      |
| GTG | CTC | GAC | ACG | CAA | GGC | AGG | ATC | ATC | GAG | GGG | CTG | TAT  | 1810
| Val | Leu | Asp | Thr | Gln | Gly | Arg | Ile | Ile | Glu | Gly | Leu | Tyr  |
|     |     | 510 |     |     |     |     | 515 |     |     |     | 520 |      |
| TGC | GTG | GGC | AAC | AAC | TCC | GCC | TCC | GTC | ATG | GCG | CCG | GCC  | 1849
| Cys | Val | Gly | Asn | Asn | Ser | Ala | Ser | Val | Met | Ala | Pro | Ala  |
|     |     |     | 525 |     |     |     |     | 530 |     |     |     |      |
| TAC | GCC | GGC | GCT | GGC | TCC | ACC | CTG | GGG | CCG | GCC | ATG | ACG  | 1888
| Tyr | Ala | Gly | Ala | Gly | Ser | Thr | Leu | Gly | Pro | Ala | Met | Thr  |
| 535 |     |     |     |     | 540 |     |     |     |     | 545 |     |      |
| TTT | GCC | TTC | CGC | GCC | GTG | GCT | GAC | ATG | GTA | GGC | AAA | CCC  | 1927
| Phe | Ala | Phe | Arg | Ala | Val | Ala | Asp | Met | Val | Gly | Lys | Pro  |
|     |     | 550 |     |     |     |     | 555 |     |     |     |     | 560  |
| TTG | CCT | CTC | GAG | AAC | CCG | CAT | CTG | CTG | GGC | AAG | ACG | GTT  | 1966
| Leu | Pro | Leu | Glu | Asn | Pro | His | Leu | Leu | Gly | Lys | Thr | Val  |
|     |     |     |     | 565 |     |     |     |     | 570 |     |     | 573  |

| | | | | |
|---|---|---|---|---|
| TGACCAGGAG | GCGCAGAGAT | GTCCAATGTC | AAAAAGCATG | TCAGCACCAT | 2016
| CAATCCTGTG | GGGGAAGTCC | TGGATGTGGG | GTCGGCCGAT | GAGGTTCAGT | 2066
| GGTCCGATGC | CAGCGATGTG | GTGGTGGTCG | GCTGGGGAGG | GGCAGGTGCC | 2116
| AGTGCAGCGA | TTGAGGCGCG | CGAGCAGGGG | GCAGAAGTTC | TGGTGATCGA | 2166
| GCGCTTCAGC | GGTGGCGGTG | CCAGTGTGCT | GTCGGGCGGT | GTGGTCTATG | 2216
| CCGGTGGCGG | TACC | | | | 2230

(2) INFORMATION FOR SEQ ID NO:2:

(i) SEQUENCE CHARACTERISTICS:
        (A) LENGTH: 573 AMINO ACIDS
        (B) TYPE: AMINO ACID
        (D) TOPOLOGY: LINEAR (ii) MOLECULE TYPE:
        (A) DESCRIPTION: PROTEIN (iii) HYPOTHETICAL: NO (iv) ANTI-SENSE: NO (vi) ORIGINAL SOURCE:
        (A) ORGANISM: PSEUDOMONAS TESTOSTERONI (ix) FEATURE: (R, repeat if necessary)
        (A) NAME/KEY: PROTEIN
        (B) LOCATION: 1..573
        (C) OTHER INFORMATION: /note =Delta
           dehydrogenase protein of Pseudomonas
           testosteroni (xi) SEQUENCE DESCRIPTION:SEQ ID NO:2:

| | | | | | | | | | | | |
|---|---|---|---|---|---|---|---|---|---|---|---|
| | | | | | | | | | Met | Ala | Glu |
| | | | | | | | | | 1 | | |
| Gln | Glu | Tyr | Asp | Leu | Ile | Val | Val | Gly | Ser | Gly | Ala | Gly |
| | 5 | | | | | 10 | | | | | 15 | |
| Ala | Cys | Trp | Ala | Pro | Ile | Arg | Ala | Gln | Glu | Gln | Gly | Leu |
| | | | 20 | | | | | 25 | | | | |
| Lys | Thr | Leu | Val | Val | Glu | Lys | Thr | Glu | Leu | Phe | Gly | Gly |
| 30 | | | | | 35 | | | | | 40 | | |
| Thr | Ser | Ala | Leu | Ser | Gly | Gly | Gly | Ile | Trp | Ile | Pro | Leu |
| | | | 45 | | | | 50 | | | | | 55 |
| Asn | Tyr | Asp | Gln | Lys | Thr | Ala | Gly | Ile | Lys | Asp | Asp | Leu |

```
                        60                            65
       Glu  Thr  Ala  Phe  Gly  Tyr  Met  Lys  Arg  Cys  Val  Arg  Gly
            70                      75                      80

Met  Ala  Thr  Asp  Asp  Arg  Val  Leu  Ala  Tyr  Val  Glu  Thr
                      85                      90

Ala  Ser  Lys  Met  Ala  Glu  Tyr  Leu  Arg  Gln  Ile  Gly  Ile
       95                      100                     105

Pro  Tyr  Arg  Ala  Met  Ala  Lys  Tyr  Ala  Asp  Tyr  Tyr  Pro
                 110                     115                          120

His  Ile  Glu  Gly  Ser  Arg  Pro  Gly  Gly  Arg  Thr  Met  Asp
                           125                     130

Pro  Val  Asp  Phe  Asn  Ala  Ala  Arg  Leu  Arg  Val  Thr  Ala
            135                     140                     145

Leu  Glu  Thr  Met  Arg  Pro  Gly  Pro  Pro  Gly  Asn  Gln  Leu
                           150                     155

Phe  Gly  Arg  Met  Ser  Ile  Ser  Ala  Phe  Glu  Ala  His  Ser
       160                     165                     170

Met  Leu  Ser  Arg  Glu  Leu  Lys  Ser  Arg  Phe  Thr  Ile  Leu
                 175                     180                          185

Gly  Ile  Met  Leu  Lys  Tyr  Phe  Leu  Asp  Tyr  Pro  Trp  Arg
                           190                     195

Asn  Lys  Thr  Arg  Arg  Asp  Arg  Arg  Met  Thr  Gly  Gly  Gln
            200                     205                     210

Ala  Leu  Val  Ala  Gly  Leu  Leu  Thr  Ala  Ala  Asn  Lys  Ala
                      215                     220

Arg  Val  Glu  Met  Trp  Cys  Asn  Ser  Pro  Leu  Lys  Glu  Leu
       225                     230                     235

Val  Gln  Asp  Ala  Ser  Gly  Arg  Val  Thr  Gly  Val  Ile  Val
                 240                     245                          250

Glu  Arg  Asn  Gly  Gln  Arg  Gln  Gln  Ile  Asn  Ala  Arg  Arg
                           255                     260

Gly  Val  Leu  Leu  Gly  Ala  Gly  Gly  Phe  Glu  Arg  Asn  Gln
            265                     270                     275

Glu  Met  Arg  Asp  Gln  Tyr  Leu  Asn  Lys  Pro  Thr  Arg  Leu
                      280                     285

Val  Asp  Gly  Asn  Pro  Cys  Gly  Arg  Gln  Tyr  Gly  Asp  Ala
       290                     295                     300

His  Arg  Ala  Gly  Gln  Ala  Trp  Ala  His  Thr  Gly  Ala  Asp
                 305                     310                          315

Gly  Leu  Val  Leu  Gly  Arg  Ala  His  His  Gly  Cys  Ser  Gln
                           320                     325

Gly  Ala  Gly  Leu  Ser  Arg  His  Phe  Arg  Gly  Thr  Leu  Ala
            330                     335                     340

Ala  Gly  Val  His  Gly  Gly  Gln  Arg  Gln  Gly  Ala  Ala  Leu
                      345                     350

Pro  Gln  Arg  Val  Arg  Pro  Val  Ser  Gly  Ile  Pro  Ala  Ala
       355                     360                     365

Met  Leu  Ala  Glu  Asn  Ala  Lys  Gly  Asn  Gly  Gly  Val  Pro
                 370                     375                          380

Ala  Trp  Ile  Val  Phe  Asp  Ala  Ser  Phe  Arg  Ala  Gln  Asp
                           385                     390

Pro  Met  Gly  Pro  Leu  Met  Pro  Gly  Ser  Ala  Val  Pro  Asp
            395                     400                     405
```

-continued

| | | | | | | | | | | | |
|---|---|---|---|---|---|---|---|---|---|---|---|
| Ser | Lys | Val | Arg 410 | Lys | Ser | Trp | Leu | Asn 415 | Asn | Val | Tyr | Trp |
| Lys 420 | Gly | Arg | Arg | Trp | Lys 425 | Ile | Trp | Arg | Ala | Asp 430 | Arg | Arg |
| Gly | Arg | Ala 435 | Gly | Leu | Gln | Val | Ser 440 | Ala | Arg | Arg | Met | Thr 445 |
| Glu | Tyr | Ala | Arg | Ala 450 | Gly | Lys | Asp | Leu | Asp 455 | Phe | Asp | Arg |
| Gly | Gly 460 | Asn | Val | Phe | Asp | Arg 465 | Tyr | Tyr | Gly | Asp | Pro 470 | Arg |
| Leu | Lys | Asn | Pro 475 | Asn | Leu | Gly | Pro | Ile 480 | Glu | Lys | Gly | Pro |
| Phe 485 | Tyr | Ala | Met | Arg | Leu 490 | Trp | Pro | Gly | Glu | Ile 495 | Gly | Thr |
| Lys | Gly | Gly 500 | Leu | Leu | Thr | Asp | Arg 505 | Glu | Gly | Arg | Val | Leu 510 |
| Asp | Thr | Gln | Gly | Arg 515 | Ile | Ile | Glu | Gly | Leu 520 | Tyr | Cys | Val |
| Gly | Asn 525 | Asn | Ser | Ala | Ser | Val 530 | Met | Ala | Pro | Ala | Tyr 535 | Ala |
| Gly | Ala | Gly | Ser 540 | Thr | Leu | Gly | Pro | Ala 545 | Met | Thr | Phe | Ala |
| Phe 550 | Arg | Ala | Val | Ala | Asp 555 | Met | Val | Gly | Lys | Pro 560 | Leu | Pro |
| Leu | Glu | Asn 565 | Pro | His | Leu | Leu | Gly 570 | Lys | Thr | Val 573 | | |